US008105613B2

(12) United States Patent
Flick-Smith et al.

(10) Patent No.: US 8,105,613 B2

(45) Date of Patent: Jan. 31, 2012

(54) VACCINE FORMULATION

(75) Inventors: Helen Claire Flick-Smith, Salisbury (GB); James Edward Eyles, Salisbury (GB); Emma Louise Waters, Salisbury (GB); Nicola Jane Walker, Salisbury (GB); Ethel Diane Williamson, Salisbury (GB); Leslie William Baillie, Salisbury (GB); Julie Miller, Salisbury (GB)

(73) Assignee: The Secretary of State for Defence (GB)

( * ) Notice: Subject to any disclaimer, the term of this patent is extended or adjusted under 35 U.S.C. 154(b) by 713 days.

(21) Appl. No.: 11/886,170

(22) PCT Filed: Mar. 10, 2006

(86) PCT No.: PCT/GB2006/000838

§ 371 (c)(1), (2), (4) Date: May 6, 2008

(87) PCT Pub. No.: WO2006/095176

PCT Pub. Date: Sep. 14, 2006

(65) Prior Publication Data

US 2010/0015181 A1 Jan. 21, 2010

(30) Foreign Application Priority Data

Mar. 10, 2005 (GB) .................................. 0504940.8

(51) Int. Cl.
*A61K 39/07* (2006.01)
*A61K 39/00* (2006.01)
*A61K 39/38* (2006.01)
*A61K 39/02* (2006.01)

(52) U.S. Cl. ................ 424/246.1; 424/184.1; 424/234.1

(58) Field of Classification Search ........................ None
See application file for complete search history.

(56) References Cited

U.S. PATENT DOCUMENTS 7,537,771 B2 * 5/2009 Williamson et al. ....... 424/246.1
7,585,426 B2 * 9/2009 Collier et al. ................ 252/8.62
7,628,982 B2 * 12/2009 Klaviniskis et al. ..... 424/93.462
2002/0150594 A1 * 10/2002 Goldman et al. .......... 424/234.1
2003/0165538 A1 * 9/2003 Goldman et al. .......... 424/204.1
2004/0171065 A1 * 9/2004 Kim et al. ...................... 435/7.1
2005/0232947 A1 * 10/2005 Cutting ...................... 424/200.1
2009/0215092 A1 * 8/2009 Love et al. .................. 435/7.32
2009/0297548 A1 * 12/2009 Kudva et al. ............... 424/190.1
2010/0015181 A1 * 1/2010 Flick-Smith et al. ...... 424/246.1

FOREIGN PATENT DOCUMENTS

WO WO 02/00232 A2 1/2002
WO WO 2006/012366 A2 2/2006

OTHER PUBLICATIONS

Driks, Microbiology and Molecular Biology Reviews, Mar. 1999, 63/1:1-20.*
Bauer et al, J. Bacteriology, Nov. 1999, 181/22:7043-7051.*
Mauriello et al, Vaccine, 22, 2004, 117-1187.*
Isticato et al, J. Bacteriology, Nov. 2001, 183/21:6294-6301.*
Liu et al, Protein Expression and Purification, 2008, 57:72-80.*
Flick-Smith et al, Infection and Immunity, Apr. 2002, 70/4:2022-2028.*
Duc et al, Infection and Immunity, May 2003, 71/5:2810-2818.*
Cybulski et al, Vaccine, 2008, 26:4927-4939.*
Cohen et al, Infection and Immunity, Aug. 2000, 68/8:4549-4558.*
Aronson, J. Bacteriology, Jan 1981, 145/1:541-547.*
Liljeqvist et al, J. Biotechnology, 1999, 73:1-33.*
Brossier, et al., 'Anthrax Spores Make an Essential Contribution to Vaccine Efficacy,' *Infection and Immunity*, 661-664 (Feb. 2002).
Cohen, et al., 'Attenuated Nontoxinogenic and Nonencapsulated Recombinant *Bacillus anthracis* Spore Vaccines Protect against Anthrax,' *Infection and Immunity*, 4549-4558 (Aug. 2000).
Grass, et al., 'Camelysin Is a Novel Surface Metalloproteinase from *Bacillus cereus,' Infection and Immunity*, 219-228 (Jan. 2004).
Kudva, et al., 'Identification of a Protein Subset of the Anthrax Spore Immunome in Humans Immunized with the Anthrax Vaccine Adsorbed Preparation,' *Infection and Immunity*, 5685-5695 (Sep. 2005).

* cited by examiner

*Primary Examiner* — Nita M Minnifield

(74) *Attorney, Agent, or Firm* — Kilpatrick Townsend & Stockton LLP

(57) ABSTRACT

Spore coat-associated proteins from members of *Bacillus* genera, and in particular spore-coat associated protein N (CotN), have utilization as adjuvants in vaccine formulations. The vaccine formulations most likely contain a virulence factor of bacterial origin, which in the case of *Bacillus* genera is the protective antigen.

20 Claims, No Drawings

VACCINE FORMULATION

CROSS REFERENCE TO RELATED APPLICATIONS

This application is the U.S. national phase of International Application No. PCT/GB2006/000838 filed on Mar. 10, 2006 and published in English on Sep. 14, 2006 as International Publication No. WO 2006/095176 A2, which application claims priority to Great Britain Patent Application No. GB 0504940.8 filed on Mar. 10, 2005, the contents of which are incorporated herein by reference.

This invention relates to vaccine formulations comprising spore coat-associated proteins from members of *Bacillus* genera as adjuvants.

The genera *Bacillus*, within the family Bacillaceae, is a group of spore forming Gram-positive bacteria, of which *Bacillus anthracis*, the causative agent of anthrax, is a member. Anthrax is primarily a disease of domesticated and wild animals, with humans becoming infected incidentally on contact with infected animals. Forms of the disease include cutaneous anthrax, often acquired through open wounds, and inhalation anthrax, moat commonly resulting from inhalation of anthrax spores. Spores are formed intacellularly by vegetative cells in response to environmental signals mat indicate a limiting factor for vegetative growth, such as exhaustion of an essential nutrient. They have proven to be the most durable type of cell found in nature and can remain visible, in this state of dormancy, for long periods of time, perhaps millions of years. They germinate and become vegetative cells when the environmental stress is relieved. Hence, spore-formation is a mechanism of survival, rather man a mechanism of reproduction. The core of the spore is surrounded by a cell wall, the cortex, and then the spore coat. Depending on the species, an exosporium may be present. The outer spore coat represents 30-60 percent of the dry weight of the spore. The spore coat proteins have an unusually high content of cysteine and of hydrophobic amino acids.

*Bacillus anthracis* produces two virulence factors, a poly-D-glutamic acid capsule and a tripartite toxin, composed of protective antigen (PA) lethal factor (LF) and Edema factor. PA is composed of four distinct and functionally independent domains, and is also the key protective component in existing vaccines to protect against anthrax infection. Nasally delivered (recombinant) protective antigen is non-immunogenic unless delivered with a mucosal adjuvant.

Disease causing organisms contain proteins called antigens which stimulate the immune response. The resulting immune response includes the synthesis of proteins called antibodies. These proteins bind to the disease causing organisms leading to eventual destruction.

The first step in making a vaccine is to isolate or create an organism, or part of one, that is unable to cause full blown disease, but that still retains the antigen responsible for inducing a protective immune response. One way is to kill the organism, for example using formalin. Vaccines produced minis way are called "inactivated" or "killed" vaccines. Another way is to use the antigen itself, for example the capsule, the flagella, or part of the protein cell wall.

Vaccines can be made by attenuation or weakening of a live microorganism by ageing or altering the growth conditions. Examples of attenuated vaccines are those that protect against measles, mumps, and rubella.

Some vaccines are made from toxins. In these cases, the toxin is often treated or modified to reduce the harmful effect. The modified/treated toxin is called a toxoid. Examples of toxoids are the diphtheria and tetanus vaccines. Vaccines made from toxoids often induce low level immune responses and are therefore sometimes administered with an adjuvant, an agent used to boost the immune response.

Vaccines may be used therapeutically in response to an exposure, or suspected exposure, to a pathogen or they may be used prophylactically to provide protection to an individual before any exposure or potential exposure occurs. Accordingly, as used herein, the term "vaccine" includes both therapeutic and prophylactic vaccines.

To elicit a strong mucosal immune response, particularly for intranasally administered antigens, an adjuvant is required. One of the most effective mucosal adjuvants is cholera toxin from *Vibric cholerae*. Cholera toxin is extremely toxic, even at low concentrations, and is unlikely to be licensed for use in human vaccines.

There is a requirement for effective mucosal adjuvants mat are not based on toxins.

According to the present invention mere is a vaccine formulation comprising a spore-coat associated protein from a member of *Bacillus* genera as adjuvant, preferably a spore-coat associated protein from a strain of *Bacillus* cereus or *Bacillus anthracis.*

The vaccine may be used as a therapeutic or prophylactic vaccine but it is preferred the vaccine is a prophylactic vaccine.

In a preferred embodiment the vaccine formulation is a live attenuated vaccine or an inactivated vaccine, and most preferably a subunit vaccine.

Adjuvants are known to increase the effectiveness of vaccines against a variety of diseases e.g. MPL™ (produced by Corixa™) adjuvant, a lipid A derivative from gram-negative bacteria, has been associated with vaccines against papillomavirus, herpes simplex virus, allergies, tuberculosis and various forms of cancer.

In one aspect of the invention, the vaccine formulation comprises a spore coat-associated protein from a member of *Bacillus* genera as adjuvant and an antigen.

Preferably, the antigen is from viral, plant or animal origin. More preferably, the antigen is capable of causing one or more diseases selected from papillomavirus, herpes simplex virus, pneumonic plague, allergies, and various forms of cancer including breast cancer and prostate cancer. Furthermore, the vaccine formulation can comprise a virulence factor of bacterial origin, preferably from a member of *Bacillus* genera, and most preferably from a stow of *Bacillus anthracis*. Alternatively, the virulence factor is from a tuberculosis causing bacteria. e.g. *M. tuberculosis*

The term 'virulence factor' denotes either an intact virulence factor, or a port thereof, throughout the entire document.

The virulence factor is preferably the protective antigen from a member of *Bacillus* genera, and most preferably the protective antigen from *Bacillus anthracis.*

In a further embodiment the virulence factor is a recombinant form of protective antigen, a mutant form of protective antigen, or a distinct and functionally independent domain of protective antigen.

The invention also discloses a vaccine formulation wherein the adjuvant and virulence factor are microencapsulated, or the adjuvant is microencapsulated, or preferably wherein the virulence factor is microencapsulated.

Delivery of the vaccine is by any suitable method. Preferably the delivery of the vaccine is by a non-parenteral route. More preferably, the delivery is by the intra-nasal route or an oral route.

Where the vaccine is suitable for oral administration e.g. in the form of a dragree, a tablet, a capsule, a spray, an aerosol, a liquid e.g. a syrup, a tincture (particularly when the pharmaceutical composition is solubilised in alcohol). The vaccine may be vaccine may be suitable for pulmonary administration e.g. in the form of an aerosol, a spray or an inhaler.

The vaccine of the invention may also be prepared in a solid form which is suitable for solubilising or suspending in a liquid. Preferably, the liquid is water or alcohol. The solid form can be a lyophilized composition or a spray freeze-dried composition. The solid form can be solubilised or suspended in liquid immediately prior to administration. Advantages of using lyophilized vaccines include economical savings because of cheaper transportation costs and easier storage conditions because the compositions tend to be more stable in a lyophilized state compared to being in solution. In such cases, the vaccine is preferably supplied as a kit that includes all or some of the components necessary for reconstitution into a form suitable to administration to a host organism. Such a kit may contain a mixture of forms, e.g. the vaccine could be in a lyophilized form and in addition, the kit would provide a liquid for solubilization or suspension of the lyophilised vaccine.

A "vaccine formulation", as used herein, can refer to either a prophylactic or a therapeutic formulation, that is, as well as protecting against disease, it is possible that the vaccine formulation can alleviate a symptom of a disease (i.e. act as a therapeutic). The present invention discloses any spore coat-associated protein from a member of *Bacillus* genera, preferably CotN from a member of *Bacillus* genera, and most preferably CotN from *Bacillus anthracis*.

The present invention also disclosed the amino acid sequence for CotN from *Bacillus anthracis* as shown in SEQ ID NO. 1, and the nucleic acid sequence, SEQ ID NO 2, encoding for CotN from *Bacillus anthracis*.

Specific embodiments of the invention will now be described by way of example.

EXAMPLE 1 a) Single, intra-nasally delivered 75 µg dose of recombinant protective antigen (rPA) microspheres administered plus 10 µg 'free' CotN protein provided substantially higher antibody titres man microspheres administered without adjuvant.
b) These antibody titres were comparable to those seen in mice given microspheres administered with 0.2 µg Cholera Toxin (CT) as an adjuvant.
c) Following challenge on day 128 post immunization with 1000 MLD of anthrax strain STI spores given by the infra-peritoneal route, mice immunised with 75 µg of microspheres alone, or with CT or CotN were all fully protected.

EXAMPLE 2 a) Single, intra-nasally delivered 50 µg dose of 'free'rPA administrated plus either 0.2 µg of CT or 10 µg of CotN provided comparable antibody titres.
b) Previous work has shown that a dose of up to 120 µg of rPA delivered intra-nasally without adjuvant does not produce a detectable antibody response.
c) Mice were challenged with 100 MLD of anthrax strain STI spores given by the intra-peritoneal route on day 90 post immunisation and were all fully protected.

EXAMPLE 3 a) Single, intra-nasally delivered 25 µg dose of rPA microspheres administered plus 10 µg 'free' CotN protein provided substantially higher antibody titres than microspheres administered with 0.2 µg CT as adjuvant or microspheres administered without adjuvant.
b) Single, intra-nasally delivered 25 µg or 10 µg dose of 'free' rPA administered plus either 0.2 µg of CT or 10 µg of CotN provided comparable antibody titres. 25 µg 'free' rPA administered without adjuvant did not produce a detectable antibody response.
c) Mice were challenged with 94 MLD of anthrax strain STI spores delivered by the aerosol route on day 80 post challenge. Mice immunised with 25 µg of rPA microspheres either alone or with CT or CotN were all fully protected against challenge.
d) Mice immunised with either 25 µg or 10 µg of 'free' rPA plus CotN had an 83% survival rate compared to 100% survival rate of mice immunised with CT as the adjuvant and a 0% survival rate of mice immunised without adjuvant.

A single dose of CotN administered intra-nasally with recombinant protective antigen (rPA) either as a microsphere (microencapsulated) formulation or as free protein enhances the immune response to the rPA antigen.

This immune response is comparable to that seen when the antigen is administered with the potent mucosal adjuvant CT and is substantially better than that seen when the antigen is delivered without adjuvant.

CotN as an adjuvant provided full protection against inject challenge and significantly better protection than control immunised mice against aerosol challenge with anthrax strain STL.

EXAMPLE 4

The methods of the previous examples can be easily adapted by a skilled artisan for use with antigens other than rPA as may be required for vaccines that are effective against diseases other than anthrax.

The rPA of example 1, therefore, could be replaced by another antigen and the resulting vaccine would particular to that disease rather than anthrax.

A vaccine formulation in accordance with the present invention is one that shows comparable or better results to that demonstrated by the same antigen but with the CT adjuvant e.g. as demonstrated in example 1, where antibody titres were compared.

The invention claimed is:

1. A vaccine formulation comprising an antigen and an adjuvant comprising an isolated spore coat-associated protein from a member of *Bacillus* genera.

2. The vaccine formulation of claim 1, wherein the member of *Bacillus* genera is *Bacillus cereus* or *Bacillus anthracis.*

3. The vaccine formulation of claim 1, wherein the vaccine formulation is a live attenuated vaccine, or an inactivated vaccine.

4. The vaccine formulation of claim 1, wherein the vaccine formulation is a subunit vaccine.

5. The vaccine formulation of claim 1, wherein the antigen is a *Bacillus* virulence factor protein.

6. The vaccine formulation of claim 5, wherein the virulence factor protein is *Bacillus anthracis* protein.

7. The vaccine formulation of claim 6, wherein the antigen is an isolated *Bacillus anthracis* protective antigen protein.

8. The vaccine formulation of claim 7, wherein the antigen is a recombinant *Bacillus anthracis* protective antigen protein.

9. The vaccine formulation of claim 1, wherein at least one of the antigen or the adjuvant is microencapsulated.

10. The vaccine formulation of claim 1, wherein the vaccine formulation is in a form suitable for administration by the intra-nasal route.

11. The vaccine formulation of claim 1, wherein the dose of adjuvant is of from about 1 ng to 100 μg, 100 ng to 10 μg, 1 ng to 1 mg, or 100 ng to 100 μg.

12. The vaccine formulation of claim 1, wherein the isolated spore coat-associated protein is spore coat-associated protein N (Cot N).

13. The vaccine formulation of claim 12, wherein the isolated spore-coat associated protein is *Bacillus anthracis* spore-coat associated protein N (CotN).

14. The vaccine formulation of claim 13, wherein the isolated spore-coat associated protein N (CotN) comprises SEQ ID NO:1.

15. The vaccine formulation of claim 13, wherein the isolated spore-associated protein N (CotN) is encoded by a nucleic acid comprising the nucleic acid sequence of SEQ ID NO:2.

16. A formulation for stimulating an immune response to an antigen in an individual comprising the antigen and an isolated spore coat-associated protein from a member of *Bacillus* genera in an amount capable of enhancing the immune response to the antigen in the individual when the formulation is administered to the individual.

17. A formulation for stimulating an immune response to an antigen in an individual comprising an antigen and an isolated spore coat-associated protein from a member of *Bacillus* genera in an amount capable of eliciting antibody titers to the antigen in the individual when the formulation is administered to the individual comparable to or higher than antibody titers seen when the antigen is administered with an adjuvant amount of cholera toxin.

18. A formulation for stimulating an immune response to an antigen in an individual comprising the antigen and an adjuvant amount of an isolated spore coat-associated protein from a member of *Bacillus* genera.

19. A method of stimulating an immune response in an individual comprising administering to the individual a vaccine formulation of claim 1.

20. A method of stimulating an immune response to anthrax infection comprising administration to an individual a vaccine formulation of claim 16.

* * * * *

SEQUENCE LISTING

```
<160> NUMBER OF SEQ ID NOS: 2

<210> SEQ ID NO 1
<211> LENGTH: 197
<212> TYPE: PRT
<213> ORGANISM: Bacillus anthracis
```

-continued

```
<400> SEQUENCE: 1

Met Ser Leu Lys Lys Lys Leu Gly Met Gly Val Ala Ser Ala Ala Leu
1               5                   10                  15

Gly Leu Ser Leu Ile Gly Gly Gly Thr Phe Ala Tyr Phe Ser Asp Lys
            20                  25                  30

Glu Val Ser Asn Asn Thr Phe Ala Ala Gly Thr Leu Asp Leu Thr Leu
        35                  40                  45

Asp Pro Lys Thr Leu Val Asp Ile Lys Asp Leu Lys Pro Gly Asp Ser
    50                  55                  60

Val Lys Lys Glu Phe Leu Leu Lys Asn Ser Gly Ser Leu Thr Ile Lys
65                  70                  75                  80

Asp Val Lys Leu Ala Thr Lys Tyr Thr Val Lys Asp Val Lys Gly Asp
                85                  90                  95

Asn Ala Gly Glu Asp Phe Gly Lys His Val Lys Val Lys Phe Leu Trp
            100                 105                 110

Asn Trp Asp Lys Gln Ser Glu Pro Val Tyr Glu Thr Thr Leu Ala Asp
        115                 120                 125

Leu Gln Lys Thr Asp Pro Asp Leu Leu Ala Gln Asp Ile Phe Ala Pro
    130                 135                 140

Glu Trp Gly Glu Lys Gly Gly Leu Glu Ala Gly Thr Glu Asp Tyr Leu
145                 150                 155                 160

Trp Val Gln Phe Glu Phe Val Asp Asp Gly Lys Asp Gln Asn Ile Phe
                165                 170                 175

Gln Gly Asp Ser Leu Asn Leu Glu Trp Thr Phe Asn Ala Asn Gln Glu
            180                 185                 190

Ala Gly Glu Glu Lys
        195


<210> SEQ ID NO 2
<211> LENGTH: 594
<212> TYPE: DNA
<213> ORGANISM: Bacillus anthracis

<400> SEQUENCE: 2

gtgagtctga aaaagaaatt aggtatggga gttgcatcag cagcattggg gttatcttta      60

attggtggag gaacatttgc ttactttagc gataaagaag tatcgaacaa tacatttgca     120

gctgggacgt tagatcttac attagaccct aaaacgcttg tagatattaa agatttaaaa     180

ccaggggatt ctgttaagaa agagttctta ttaaagaata gcggttcatt aacaattaaa     240

gacgttaaac tagcaacaaa gtatactgtg aaagatgtaa aaggtgataa tgctggtgaa     300

gactttggta agcacgttaa agtgaaattc ctttggaact gggataaaca aagtgagcct     360

gtatatgaaa caactttagc agacttacaa aaaactgatc cagatctttt agctcaagac     420

atttttgctc ctgagtgggg ggaaaagggt ggattagaag ctggtaccga ggattattta     480

tgggtacaat ttgaatttgt agatgatgga aaagaccaaa atatcttcca aggtgattca     540

ttgaatttag aatggacatt caatgctaac caagaagctg gagaagaaaa ataa           594
```